US012692244B2

(12) United States Patent
Bai et al.

(10) Patent No.: US 12,692,244 B2
(45) Date of Patent: Jul. 28, 2026

(54) GRISEOFULVIN 4 POSITION ETHERIFIED DERIVATIVES AND THEIR APPLICATION

(71) Applicant: Yan'an University, Yan'an (CN)

(72) Inventors: Yubin Bai, Yan'an (CN); Meng Zhang, Yan'an (CN); Liangzhu Huang, Yan'an (CN); Yu Zhao, Yan'an (CN)

(73) Assignee: Yan'an University, Yan'an (CN)

( * ) Notice: Subject to any disclaimer, the term of this patent is extended or adjusted under 35 U.S.C. 154(b) by 351 days.

(21) Appl. No.: 18/413,049

(22) Filed: Jan. 16, 2024

(65) Prior Publication Data

US 2024/0294486 A1 Sep. 5, 2024

(30) Foreign Application Priority Data

Feb. 20, 2023 (CN) ......................... 202310137378.5

(51) Int. Cl.
*C07D 307/94* (2006.01)
*A01N 43/08* (2006.01)

(52) U.S. Cl.
CPC .................................. *C07D 307/94* (2013.01)

(58) Field of Classification Search
CPC .......... C07D 307/94; A01P 3/00; A01N 43/08
USPC ........................................... 549/345; 504/140
See application file for complete search history.

(56) References Cited

FOREIGN PATENT DOCUMENTS

CN 108779089 A 11/2018

OTHER PUBLICATIONS

Crosse, R. et al.: Some relationship between chemical structure and antifungal effectes of griseofulvin analogs. Journal of General Microbiology, vol. 34, pp. 51-65, 1964.*

Dhanshri C Juvale et al., "Comparative 2D and 3D-QSAR of antifungal griseofuivin analogues," Indian Journal of Chemistry, vol. 45A. Jan. 2006, pp. 194-201.

* cited by examiner

*Primary Examiner* — Charanjit Aulakh
(74) *Attorney, Agent, or Firm* — Hemisphere Law, PLLC

(57) ABSTRACT

Provided are griseofulvin 4 position etherified derivatives and their application thereof. The chemical structures of the griseofulvin 4 position etherified derivatives are drawn in a formula I below. The application of these derivatives includes using the griseofulvin 4 position etherified derivatives as preventive or direct antifungal agents against phytopathogenic fungi.

I

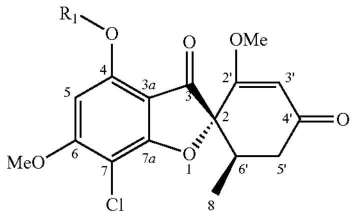

8 Claims, No Drawings

GRISEOFULVIN 4 POSITION ETHERIFIED DERIVATIVES AND THEIR APPLICATION

TECHNICAL FIELD

The present disclosure is about griseofulvin 4 position etherified derivatives and their application, including griseofulvin 4 position etherified derivatives, synthetic procedure, and antifungal application against phytopathogenic fungi.

BACKGROUND

Griseofulvin, a natural product, which was isolated from fungal mycelium of *penicillium griseofulvum* in 1939. Since it was isolated, hundreds of griseofulvin derivatives have been used for drug screening. (McBride, B. C. 1965, Doctoral dissertation, University of British Columbia.), It was used as an antifungal drug for dermatomycoses. (Arkley, V., Attenburrow, J., Gregory, G. I., & Walker, T. J. *Chem. Soc.* (*Resumed*). 1962, 1260-1268.).

In recent years, there are some new references reported that griseofulvin derivatives have antifungal activity against phytopathogenic fungi and some anticancer activity. (Petersen, A. B., Andersen, N. S., Konotop, G., Hanafiah, N. H. M., Raab, M. S., Krämer A., & Clausen, M. H. Eur. J. Med. Chem. 2017, 130, 240-247.; Bai, Y-B., Gao, Y-Q., Nie, X-D., Tuong, T.-M.-L., Li, D., Gao, J.-M. J. *Agric. Food. Chem.* 2019, 67(22), 6125-6132.).

THE CONTENTS

A series of griseofulvin 4 position etherified derivatives are provided in the present disclosure. General chemical structures of griseofulvin 4 position etherified derivatives are shown in a formula I as below.

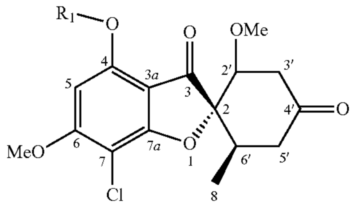

I

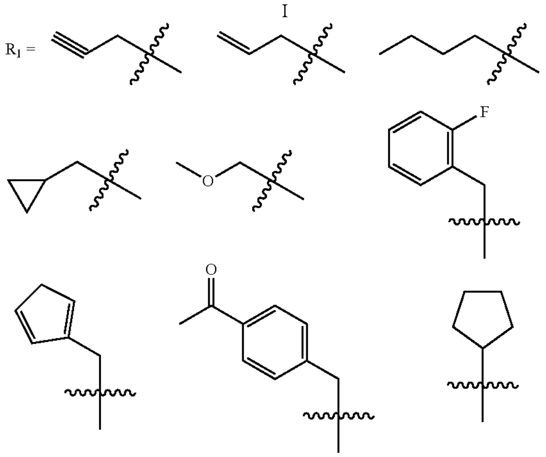

The preparation method of the synthesis of griseofulvin 4 position etherified derivatives is provided, which includes:

with organic solvent and base, intermediate II reacted with different bromoalkanes, griseofulvin 4 position etherified derivatives were obtained, a chemical structure of the intermediate II is shown below.

II

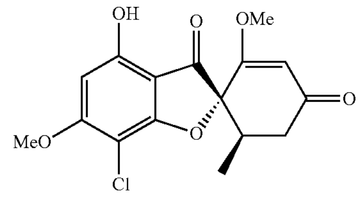

The appropriate methods could be used to obtain the desired product, for example the preparation method included but not limited that after the reaction finished, the reaction mixture was concentrated and purified by column chromatography in order, to get the desired product griseofulvin 4 position etherified derivatives.

Griseofulvin 4 position etherified derivatives can be used to be preventive or direct fungicide agents against phytopathogenic fungi in present disclosure. The phytopathogenic Fungi includes one or more of *Cytospora* sp., *Alternaria solani Sorauer, Alternaria* alternate, *Botrytis* sp., *Botrytis cinerea* Pers., *Colletotrichum gloeosporioides*, or *Botryosphaeria dothidea.*

THE SPECIFIC PROCEDURE

The scientific and technical words in this document is based on the understanding of the common technicians in relative field, except where noted.

The chemical structures of griseofulvin derivatives (compound 01, 02, 03, 04, 05, 06, 07, 08 and 09) are drawn below.

01

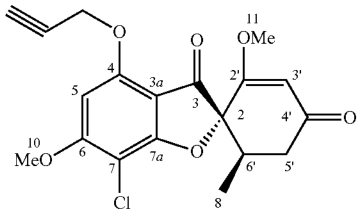 [SMILES: C#CCOc1cc(OC)c(Cl)c2c1C(=O)[C@@]1(O2)C(OC)=CC(=O)C[C@H]1C]

02

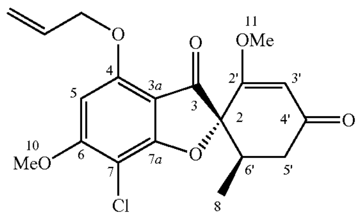 [SMILES: C=CCOc1cc(OC)c(Cl)c2c1C(=O)[C@@]1(O2)C(OC)=CC(=O)C[C@H]1C]

03

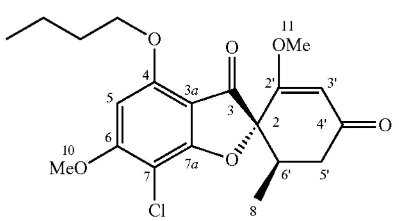 [SMILES: CCCCOc1cc(OC)c(Cl)c2c1C(=O)[C@@]1(O2)C(OC)=CC(=O)C[C@H]1C]

-continued

04

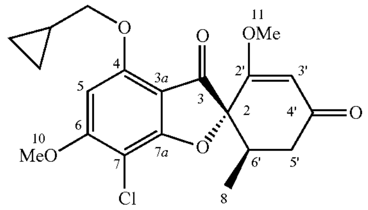 [SMILES: COC1=CC(=O)C[C@@H](C)[C@]12Oc1c(Cl)c(OC)cc(OCC3CC3)c1C2=O]

05

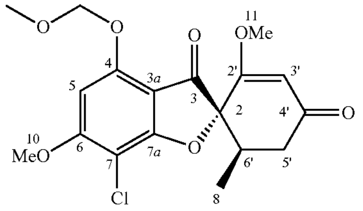 [SMILES: COCOc1cc(OC)c(Cl)c2c1C(=O)[C@@]1(O2)C(OC)=CC(=O)C[C@H]1C]

06

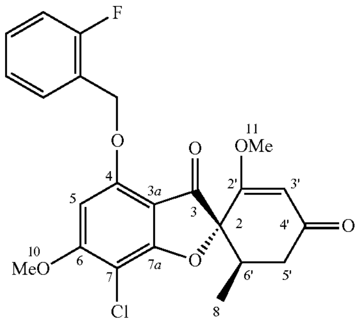 [SMILES: COC1=CC(=O)C[C@@H](C)[C@]12Oc1c(Cl)c(OC)cc(OCc3ccccc3F)c1C2=O]

07

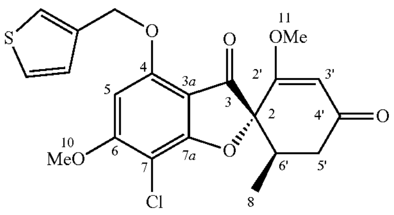 [SMILES: COC1=CC(=O)C[C@@H](C)[C@]12Oc1c(Cl)c(OC)cc(OCc3ccsc3)c1C2=O]

08

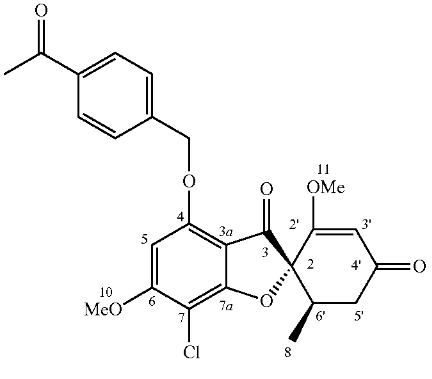 [SMILES: COC1=CC(=O)C[C@@H](C)[C@]12Oc1c(Cl)c(OC)cc(OCc3ccc(C(C)=O)cc3)c1C2=O]

-continued

09

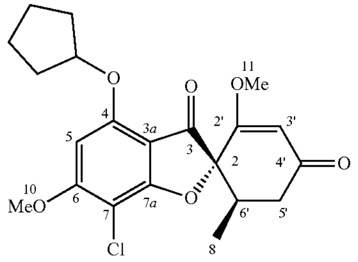

The synthetic route of griseofulvin 4 position etherified derivatives are shown below.

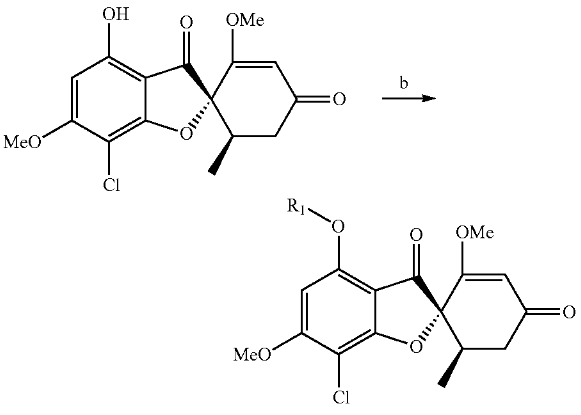

I

Reaction condition: (b) bromoalkene, base, organic solvent

General procedure for the synthesis of griseofulvin 4 position etherified derivatives. With organic solvent and base, intermediate II reacted with different bromoalkanes, griseofulvin 4 position etherified derivatives were obtained. After reaction finished, the reaction mixture was concentrated and purified by column chromatography, the desired product griseofulvin 4 position etherified derivatives were obtained. In synthesis procedure, the researchers can choose appropriate organic solvent and base. The organic solvent was but was not limited to acetone and THE et al; The base could be, but was not limited to $K_2CO_3$, $Na_2CO_3$, $Cs_2CO_3$ et al.

In this work, intermediate II was obtained by $MgI_2$, which can selectively remove the methyl of griseofulvin at position 4, and chemical structure of intermediate II was shown as below.

II

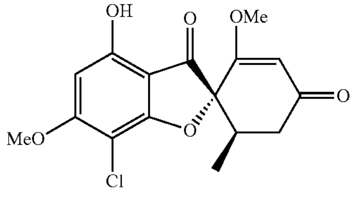

The synthesis procedure referenced a reported method (Bai Yu-Bin, Gao Yu-Qi, Nie Xiao-Di, Tuong Thi-Mai-Luong, Li Ding, Gao Jin-Ming. *J. Agric. Food. Chem.* 2019, 67 (22), 6125-6132.; Rønnest M H., Harris P., Gotfredsen C H., et al. Tetrahedron Letters. 2010, 51(45), 5881-5882.).

The procedure for the synthesis of intermediate II as follows.

The magnesium turnings (0.518 g, 21.6 mmol) and iodine (1.828 g, 7.2 mmol) were added to a solution of anhydrous $Et_2O$ (4 mL) and toluene (8 mL) under argon. And the solution was refluxed at 80° C. for 30 min until the mixture turned to be a colorless solution, then the resulting solution was added to a solution of griseofulvin (1.411 g, 4 mmol) in dry toluene (10 mL), and heated to 80° C. for 4 h, $H_2O$ (20 mL) and $Na_2S_2O_3$ were added, and the mixture was poured into 5% hydrochloric acid (10 mL) and extracted with EtOAc (3×20 mL), dried under $MgSO_4$, and concentrated. The residue was purified by column chromatography ($CH_2Cl_2$: MeOH: AcOH=97:2:1), a white solid was obtained and the yield is more than 80%.

The chemical structure of start material griseofulvin was shown below.

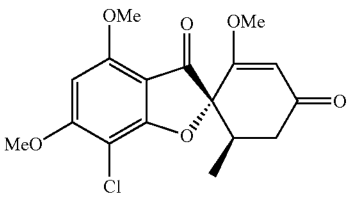

Griseofulvin

The start material griseofulvin (Cas No., 126-07-8; purity, 97%) were purchased from commercial sources (Aladdin Reagent Company).

The examples of synthesis procedure of griseofulvin 4 position etherified derivatives were shown below. The temperature and concentration are approximate value. In specific procedure, technician could choose appropriate reagent ratio, concentration, temperature (room temperature to boiling point of the solvent), solvent, reagent adding order, heating method and purify method to obtain the desired products in this document.

Example 1: The Synthesis Procedure of 4 Position Propargyl Griseofulvin Derivative (Compound 01)

The intermediate II (0.5 mmol) was dissolved in dry acetone (6 mL) solution at room temperature, then propargyl bromide (0.6 mmol) and $K_2CO_3$ (0.75 mmol) were added, reaction mixture were refluxed in oil bath, TLC monitored, after reaction finished, concentrated by rotavapor, and residue was purified by column chromatography on silica gel eluting with $CH_2Cl_2$: $CH_3OH$ (40:1-100:1), white solid was obtained, yield 95%, m.p. 176-178° C. $^1$H NMR (400 MHZ, $CDCl_3$) δ 6.37 (s, 1H, H-5), 5.54 (s, 1H, H-3'), 4.96-4.84 (m, 2H, —$OCH_2$—), 4.03 (s, 3H, H-10), 3.62 (s, 3H, H-11), 3.02 (dd, J=16.5, 13.5 Hz, 1H, H-5'), 2.89-2.79 (m, 1H, H-6'), 2.63 (s, 1H, CH≡C—), 2.43 (dd, J=16.6, 4.6 Hz, 1H, H-5'), 0.96 (d, J=6.7 Hz, 3H, H-8). $^{13}$C NMR (100 MHZ, $CDCl_3$) δ 197.17 (C-4'), 192.48 (C-3), 170.83 (C-2'), 169.65 (C-7a), 164.40 (C-6), 155.42 (C-4), 105.63 (C-3a), 105.02 (C-3'), 98.25 (C-7), 91.92 (C-5), 90.92 (C-2), 77.68 (CH≡C—), 77.08 (CH≡C—), 57.27 (—$OCH_2$—), 57.21 (C-10), 56.84 (C-11), 40.13 (C-5'), 36.57 in (C-6'), 14.38 (C-8). HR-MS (ESI): m/z calcd. for $C_{19}H_{17}ClO_6H$: 376.0714; found: 377.0792 $[M+H]^+$.

Chemical structure of compound 01 was shown below.

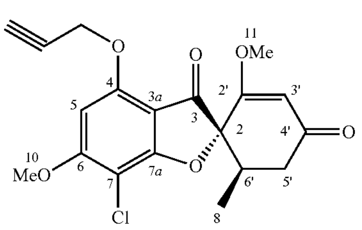

Example 2: The Synthesis Procedure of 4 Position Allyl Griseofulvin Derivative (Compound 02)

The different in this procedure is that the bromoalkene is allyl bromide, and a white solid was obtained. Yield 72%, m.p. 200-202° C.; $^1$H NMR (400 MHZ, $CDCl_3$) δ 6.14 (s, 1H, H-5), 6.11-6.01 (m, 1H, $CH_2$═CH—), 5.56-5.46 (m, 2H, H-3', —CH—$CH_2$), 5.36 (dd, J=10.5, 1.4 Hz, 1H, —CH—$CH_2$), 4.71 (d, J=5.2 Hz, 2H, —$OCH_2$—), 3.99 (s, 3H, H-10), 3.61 (s, 3H, H-11), 3.03 (dd, J=16.7, 13.5 Hz, 1H, H-5'), 2.88-2.80 (m, 1H, H-6'), 2.44-2.39 (m, 1H, H-5'), 0.96 (d, J=6.7 Hz, 3H, H-8). $^{13}$C NMR (100 MHZ, $CDCl_3$) δ 197.20 (C-4'), 192.34 (C-3), 170.97 (C-2'), 169.57 (C-7a), 164.47 (C-6), 156.85 (C-4), 131.74 ($CH_2$═CH—), 118.94 ($CH_2$═CH—), 105.45 (C-3a), 104.91 (C-3'), 97.34 (C-7), 91.02 (C-5), 90.81 (C-2), 70.17 (—$OCH_2$—), 57.08 (C-10), 56.80 (C-11), 40.11 (C-5'), 36.58 (C-6'), 14.35 (C-8). HR-MS (ESI): m/z calcd. for $C_{19}H_{19}ClO_6Na$: 401.0768; found: 401.0779 $[M+Na]^+$.

Chemical structure of compound 02 was shown below.

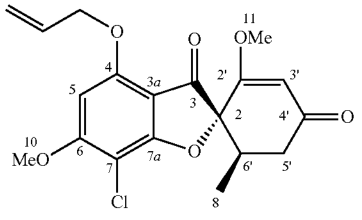

Example 3: The Synthesis Procedure of 4 Position Butyl Griseofulvin Derivative (Compound 03)

The different in this procedure is that the bromoalkene is butyl bromide, and a white solid was obtained. Yield 86%, m.p. 145-146° C.; $^1$H NMR (400 MHZ, $CDCl_3$) δ 6.11 (s, 1H, H-5), 5.53 (s, 1H, H-3'), 4.16-4.06 (m, 2H, —$OCH_2$—), 4.00 (s, 3H, H-10), 3.61 (s, 3H, H-11), 3.05 (dd, J-16.7, 13.5 Hz, 1H, H-5'), 2.86-2.80 (m, 1H, H-6'), 2.41 (dd, J=16.7, 4.7 Hz, 1H, H-5'), 1.90-1.83 (m, 2H, —$CH_2$—), 1.57-1.48 (m, 2H, —$CH_2$—), 1.05-0.90 (m, 6H, H-8, —$CH_3$). $^{13}$C NMR (100 MHz, $CDCl_3$) δ 197.23 (C-4'), 192.25 (C-3), 171.08 (C-2'), 169.58 (C-7a), 164.55 (C-6), 157.62 (C-4), 105.32 (C-3a), 104.90 (C-3'), 96.95 (C-7), 90.75 (C-5), 90.38 (C-2), 69.34 (—$OCH_2$—), 57.08 (C-10), 56.79 (C-11), 40.13 (C-5'), 36.63 (C-6'), 30.90 (—$CH_2$—), 19.21 (—$CH_2$—), 14.37 (C-8), 13.95 (—$CH_3$). HR-MS (ESI): m/z calcd. for $C_{20}H_{23}ClO_6Na$: 417.1081; found: 417.1086 $[M+Na]^+$.

Chemical structure of compound 03 was shown below.

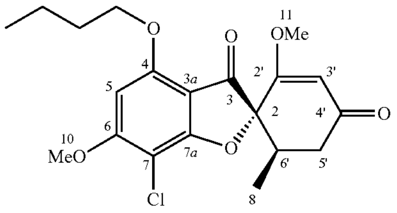

Example 4: The Synthesis Procedure of 4 Position Cyclopropylmethyl Griseofulvin Derivative (Compound 04)

The different in this procedure is that the bromoalkene is cyclopropylmethyl bromide, and a white solid was obtained. Yield 60%, m.p. 174-176° C.; $^{1}$H NMR (400 MHZ, $CDCl_3$) δ 6.10 (s, 1H, H-5), 5.53 (s, 1H, H-3'), 4.04-3.89 (m, 5H, —$OCH_2$—, H-10), 3.62 (s, 3H, H-11), 3.05 (dd, J=16.7, 13.5 Hz, 1H, H-5'), 2.87-2.80 (m, 1H, H-6'), 2.41 (dd, J=16.7, 4.7 Hz, 1H, H-5'), 1.37-1.32 (m, 1H, —CH—$C_2H_4$), 0.96 (d, J=6.7 Hz, 3H, H-8), 0.76-0.62 (m, 2H, —$CH_2$—), 0.42-0.38 (m, 2H, —$CH_2$—). $^{13}$C NMR (100 MHZ, $CDCl_3$) δ 197.24 (C-4'), 192.24 (C-3), 171.08 (C-2'), 169.61 (C-7a), 164.50 (C-6), 157.48 (C-4), 105.45 (C-3a), 104.89 (C-3'), 97.12 (C-7), 90.88 (C-5), 90.74 (C-2), 74.42 (—$OCH_2$—), 57.09 (C-10), 56.78 (C-11), 40.12 (C-5'), 36.65 (C-6'), 14.37 (C-8), 9.92 (—CH—$C_2H_4$), 3.66 (—$CH_2$—), 3.62 (—$CH_2$—). HR-MS (ESI): m/z calcd. for $C_{20}H_{21}ClO_6Na$: 415.0924; found: 415.0928 $[M+Na]^+$.

Chemical structure of compound 04 was shown below.

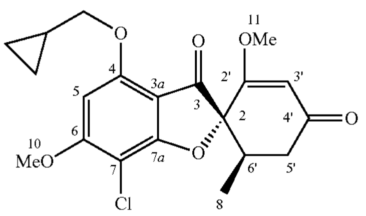

Example 5: The Synthesis Procedure of 4 Position Methoxymethyl Griseofulvin Derivative (Compound 05)

The different in this procedure is that the bromoalkene is methoxymethyl bromide, and a white solid was obtained. Yield 67%, m.p.124-125° C.; $^{1}$H NMR (400 MHZ, $CDCl_3$) δ 6.48 (s, 1H, H-5), 5.55 (s, 1H, H-3'), 5.33 (s, 2H, —$OCH_2O$—), 4.00 (s, 3H, H-10), 3.63 (s, 3H, H-11), 3.53 (s, 3H, —$OCH_3$), 3.02 (dd, J=16.5, 13.5 Hz, 1H, H-5'), 2.90-2.81 (m, 1H, H-6'), 2.43 (dd, J=16.6, 4.6 Hz, 1H, H-5'), 0.96 (d, J=6.6 Hz, 3H, H-8). $^{13}$C NMR (100 MHZ, $CDCl_3$) δ 197.21 (C-4'), 192.65 (C-3), 170.94 (C-2'), 169.44 (C-7a), 164.53 (C-6), 155.53 (C-4), 105.75 (C-3a), 104.99 (C-3'), 98.31 (C-7), 95.49 (C-5), 93.27 (—$OCH_2O$—), 90.83 (C-2), 57.24 (C-10), 57.11 (—$OCH_3$), 56.84 (C-11), 40.11 (C-5'), 36.61 (C-6'), 14.40 (C-8). HR-MS (ESI): m/z calcd. for $C_{18}H_{19}ClO_7Na$: 405.0717; found: 405.0728 $[M+Na]^+$.

Chemical structure of compound 05 was shown below.

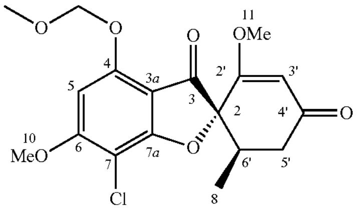

Example 6: The Synthesis Procedure of 4 Position 2-Fluorobenzyl Griseofulvin Derivative (Compound 06)

The different in this procedure is that the bromoalkene is 2-fluorobenzyl bromide, and a white solid was obtained. Yield, 83%, m.p. 212-213° C.; $^{1}$H NMR (400 MHZ, $CDCl_3$) δ 7.71-7.64 (m, 1H, ArH), 7.37-7.29 (m, 1H, ArH), 7.19 (d, J=1.0 Hz, 1H, ArH), 7.12-7.04 (m, 1H, ArH), 6.25 (s, 1H, H-5), 5.54 (s, 1H, H-3'), 5.31 (s, 2H, —$OCH_2$—), 3.99 (s, 3H, H-10), 3.62 (s, 3H, H-11), 3.04 (dd, J=16.6, 13.5 Hz, 1H, H-5'), 2.92-2.79 (m, 1H, H-6'), 2.43 (dd, J-16.7, 4.7 Hz, 1H, H-5'), 0.96 (d, J=6.7 Hz, 3H, H-8). $^{13}$C NMR (100 MHZ, $CDCl_3$) δ 197.08 (C-4'), 192.31 (C-3), 170.92 (C-2'), 169.64 (C-7a), 164.57 (C-6), 161.26 (C-4), 158.82 (C-3a), 156.43 (C-3'), 130.24 (d, J=8.2 Hz, ArC), 129.58 (d, J=3.5 Hz, ArC), 124.97 (d, J=3.7 Hz, ArC), 122.68 (d, J=13.6 Hz, ArC), 115.32 (d, J=21.0 Hz, ArC), 104.97(C-7), 105.99-96.49 (m, ArC), 91.20 (C-5), 90.89 (C-2), 64.55 (d, J=4.5 Hz, —$OCH_2$—), 57.16 (C-10), 56.80 (C-11), 40.16 (C-5'), 36.62 (C-6'), 14.38 (C-8). HR-MS (ESI): m/z calcd. for $C_{23}H_{20}ClFO_6Na$: 469.0830; found: 469.0832 $[M+Na]^+$.

Chemical structure of compound 06 was shown below.

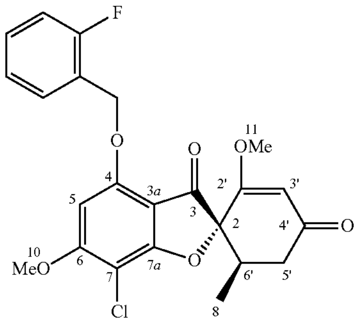

Example 7: The Synthesis Procedure of 4 Position 3-Methylthiophene Griseofulvin Derivative (Compound 07)

The different in this procedure is that the bromoalkene is 3-bromomethylthiophene, and a white solid was obtained. Yield, 73%, m.p. 212-214° C.; $^{1}$H NMR (400 MHZ, $CDCl_3$) δ 7.42-7.39 (m, 1H, —S—CH═), 7.35 (dd, J=5.0, 3.0 Hz, 1H, —S—CH≡CH—), 7.17 (dd, J=5.0, 1.3 Hz, —S—CH—CH—), 6.18 (s, 1H, H-5), 5.54 (s, 1H, H-3'), 5.27 (dd, J=2.6, 1.0 Hz, 2H, —$OCH_2$—), 3.96 (s, 3H, H-10), 3.62 (s, 3H, H-11), 3.04 (dd, J=16.7, 13.5 Hz, 1H, H-5'), 2.89-2.81 (m, 1H, H-6'), 2.45-2.40 (m, 1H, H-5'), 0.96 (d, J=6.7 Hz, 3H, H-8). $^{13}$C NMR (100 MHz, $CDCl_3$) δ 197.15 (C-4'), 192.32 (C-3), 170.95 (C-2'), 169.58 (C-7a), 164.45 (C-6), 156.74

(C-4), 136.41 (—S—CH═), 126.97 (—S—CH≡CH—), 126.42 (—S—CH—CH—), 123.22 (—S—CH—C—), 105.61 (C-3a), 104.94 (C-3'), 97.58 (C-7), 91.42 (C-5), 90.85 (C-2), 67.44 (—$OCH_2$—), 57.10 (C-10), 56.81 (C-11), 40.12 (C-5'), 36.60 (C-6'), 14.37 (C-8). HR-MS (ESI): m/z calcd. for $C_{21}H_{19}ClO_6SNa$: 457.0489; found: 457.0488 $[M+Na]^+$.

Chemical structure of compound 07 was shown below.

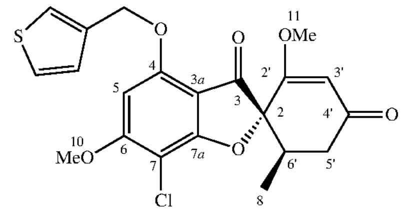

Example 8: The Synthesis Procedure of 4 Position 1-(4-(Methyl)Phenyl)-Ethanone Griseofulvin Derivative (Compound 08)

The different in this procedure is that the bromoalkene is 1-(4-(Bromomethyl)-phenyl)ethanone, and a white solid was obtained. Yield, 55%, m.p. 275-276° C.; $^1H$ NMR (400 MHZ, $CDCl_3$) δ 7.99 (d, J=8.4 Hz, 2H, ArHx2), 7.59 (d, J=8.5 Hz, 2H, ArH×2), 6.16 (s, 1H, H-5), 5.55 (s, 1H, H-3'), 5.31 (s, 2H, —$OCH_2$—), 3.96 (s, 3H, H-10), 3.63 (s, 3H, H-11), 3.04 (dd, J=16.7, 13.5 Hz, 1H, H-5'), 2.91-2.79 (m, 1H, H-6'), 2.60 (s, 3H, —$CH_3$), 2.42 (d, J=4.6 Hz, 1H, H-5'), 0.97 (d, J=6.6 Hz, 3H, H-8). $^{13}C$ NMR (100 MHZ, $CDCl_3$) δ 197.73 (—CO—), 197.01 (C-4'), 192.37 (C-3), 170.84 (C-2'), 169.67 (C-7a), 164.52 (C-6), 156.38 (ArC), 140.71 (C-4), 137.08 (ArC), 128.98 (ArC), 126.80 (ArC), 105.67 (C-3a), 105.01 (C-3'), 97.99 (C-7), 91.43 (C-5), 90.96 (C-2), 70.44 (—$OCH_2$—), 57.14 (C-10), 56.83 (C-11), 40.15 (C-5'), 36.61 (C-6'), 26.80 (—$CH_3$), 14.39 (C-8). HR-MS (ESI): m/z calcd. for $C_{25}H_{23}ClO_7Na$: 493.1030; found: 493.1035 $[M+Na]^+$.

Chemical structure of compound 08 was shown below.

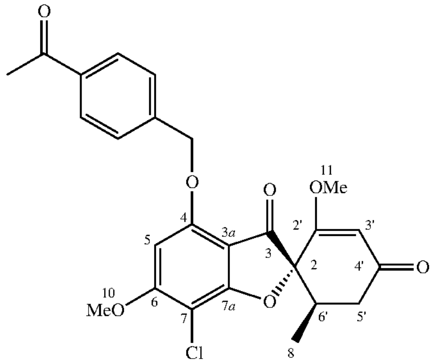

Example 9: The Synthesis Procedure of 4 Position Cyclopentyl Griseofulvin Derivative (Compound 09)

The different in this procedure is that the bromoalkene is Bromocyclopentane, and a white solid was obtained. Yield, 43%, m.p. 202-204° C.; $^1H$ NMR (400 MHz, $CDCl_3$) δ 6.11 (s, 1H, H-5), 5.52 (s, 1H, H-3'), 4.90-4.87 (m, 1H, —OCH—), 3.99 (s, 3H, H-10), 3.61 (s, 3H, H-11), 3.04 (dd, J=16.7, 13.5 Hz, 1H, H-5'), 2.85-2.81 (m, 1H, H-6'), 2.43-2.37 (m, 1H, H-5'), 2.04-1.90 (m, 4H, —$CH_2$—×2), 1.90-1.77 (m, 2H, —$CH_2$—), 1.69-1.58 (m, 2H, —$CH_2$—), 0.95 (d, J=6.7 Hz, 3H, H-8). $^{13}C$ NMR (100 MHZ, $CDCl_3$) δ 197.23 (C-4'), 192.19 (C-3), 171.16 (C-2'), 169.65 (C-7a), 164.32 (C-6), 156.82 (C-4), 105.69 (C-3a), 104.82 (C-3'), 96.69 (C-7), 91.83 (C-5), 90.67 (C-2), 81.67 (—OCH—), 57.01 (C-10), 56.77 (C-11), 40.10 (C-5'), 36.65 (C-6'), 33.02 ($CH_2$—), 32.88 (—$CH_2$—), 24.19 (—$CH_2$—), 24.17 (—$CH_2$—), 14.37 (C-8). HR-MS (ESI): m/z calcd. for $C_{21}H_{23}ClO_6Na$: 429.1081; found: 429.1087 $[M+Na]^+$.

Chemical structure of compound 09 was shown below.

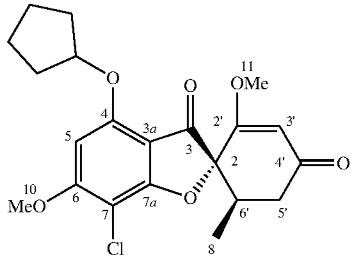 [SMILES: COC1=CC(=O)C[C@@H](C)[C@]12Oc1c(Cl)c(OC)cc(OC3CCCC3)c1C2=O]

Example 10: Antifungal Activity Assay

The antifungal activities were evaluated against seven plant phytopathogenic fungi, by the mycelial growth inhibitory rate method, according to a reported method (Yu-Bin Bai, Meng Zhang, Ding Li, Yu Zhao, Liang-Zhu Huang, and Jin-Ming Gao. *J. Agric. Food. Chem.*, 2023, 71, 16, 6236-6248). The target phytopathogenic fungi are *Cytospora* sp., *Alternaria solani Sorauer, Alternaria* alternate, *Botrytis* sp., *Botrytis cinerea* Pers., *Colletotrichum gloeosporioides* and *Botryosphaeria dothidea.* 100 μg/mL PDA mediums were prepared at 50° C. The petri dishes were incubated and cultivated at 28° C. for 48-72 h. Each sample was measured in triplicate, each colony diameter of all triplicates was measured 4 times by cross bracketing method. Hymexazol (Hym) as the positive control and the result of inhibition rate was calculated according to the formula:

$$\text{Inhibition rate}(\%) = (C - T)/(C - 4\,\text{mm}) \times 100\%,$$

where C represents the diameter of fungal growth on untreated PDA, and T represents the diameter of fungal growth on treated PDA. The results are reported in Table 1. The activity results suggested these 9 griseofulvin derivatives exhibited very excellent antifungal activity.

TABLE 1

Preliminary antifungal activity of compounds at 100 μg/mL

| | Average values of antifungal rate (%) | | | | | | |
|---|---|---|---|---|---|---|---|
| Compd | C.s. | A.s. | A.a. | B.s. | B.c. | C.g. | B.d. |
| 01 | 96.62 | 100.00 | 97.41 | 100.00 | 98.61 | 91.34 | 97.99 |
| 02 | 52.70 | 77.05 | 49.14 | 85.23 | 56.94 | 70.08 | 51.68 |
| 03 | 29.05 | 26.92 | 7.41 | 62.26 | 19.05 | 68.42 | 31.75 |

TABLE 1-continued

Preliminary antifungal activity of compounds at 100 μg/mL

| Compd | Average values of antifungal rate (%) | | | | | | |
|---|---|---|---|---|---|---|---|
| | C.s. | A.s. | A.a. | B.s. | B.c. | C.g. | B.d. |
| 04 | 65.54 | 70.49 | 41.38 | 69.80 | 50.69 | 48.03 | 26.17 |
| 05 | 73.65 | 75.41 | 49.14 | 88.59 | 65.97 | 71.65 | 58.39 |
| 06 | 6.08 | 13.11 | 3.45 | 69.80 | 55.56 | 75.59 | 18.12 |
| 07 | 54.73 | 62.30 | 43.10 | 73.83 | 59.72 | 72.44 | 42.28 |
| 08 | 7.43 | 0.00 | 2.59 | 47.65 | 43.06 | 25.98 | 4.70 |
| 09 | 59.46 | 45.90 | 31.03 | 63.09 | 59.72 | 40.94 | 34.23 |
| Hym | 48.04 | 97.44 | 92.59 | 92.45 | 100.00 | 43.16 | 55.56 |

Note:
C.s., *Cytospora* sp.;
A.s., *Alternaria solani Soraue*;
A.a., *Alternaria alternate*;
B.s., *Botrytis* sp.;
B.c., *Botrytis cinerea Pers.*;
C.g., *Colletotrichum gloeosporioides*;
B.d., *Botryosphaeria dothidea*;
Hym., *Hymexazol.*

The compounds with inhibition rates superior to 70% at 100 μg/mL were chosen. PDA mediums with different compound concentrations (100, 50, 25, 12.5, 6.25, 3.125, 1.5625, 0.78125, 0.3906, 0.1953, 0.0977, 0.0488 μg/mL) was prepared and their half inhibitory concentration ($IC_{50}$) values were accurately tested. All half inhibitory concentration results are shown in Table 2 and Hymexazol (Hym) as the positive control.

TABLE 2

The half inhibitory concentration values of antifungal activity

| Compd | $IC_{50}$ ± SD/(μg/mL) | | | | | | |
|---|---|---|---|---|---|---|---|
| | C.s. | A.s. | A.a. | B.s. | B.c. | C.g. | B.d. |
| 01 | 1.84 ± 0.01 | 1.32 ± 0.01 | 1.28 ± 0.00 | 2.84 ± 0.22 | 2.04 ± 0.12 | 0.06 ± 0.02 | 1.35 ± 0.07 |
| 02 | >50 | 14.87 ± 5.66 | >100 | 3.93 ± 0.80 | >50 | 4.05 ± 0.46 | >50 |
| 03 | >100 | >100 | >100 | >25 | >100 | >25 | >100 |
| 04 | >50 | 17.85 ± 0.04 | >25 | >100 | >100 | >100 | >100 |
| 05 | 81.41 ± 1.23 | 83.21 ± 14.50 | >50 | 31.56 ± 7.30 | >25 | 16.15 ± 1.30 | >25 |
| 06 | >100 | >100 | >100 | >25 | >50 | 1.92 ± 0.19 | >100 |
| 07 | >50 | >50 | >100 | 17.58 ± 0.27 | >25 | 3.82 ± 0.09 | >50 |
| 08 | >100 | >100 | >100 | >100 | >100 | >100 | >100 |
| 09 | >25 | >100 | >100 | >25 | >25 | >100 | >100 |
| Hym | >100 | 45.29 ± 14.04 | 15.58 ± 0.13 | 13.48 ± 1.89 | >6.25 | >100 | >50 |

The activity results suggested that compared with the positive control hymexazol and thifluzamide, these 9 griseofulvin derivatives showed very excellent antifungal activity against phytopathogenic fungi. To our surprise, compound 01 exhibited significant and extensive antifungal activity against all these seven target fungi, and their $IC_{50}$ values are respectively 1.84±0.01 μg/mL, 1.32±0.01 μg/mL, 1.28±0.00 μg/mL, 2.84±0.22 μg/mL, 2.04±0.12 μg/mL, 0.06±0.02 μg/mL, 1.35±0.07 μg/mL, particularly against *Colletotrichum gloeosporioides* ($IC_{50}$=0.06±0.02 μg/mL). Furthermore, compounds 02, 06 and 07 also showed remarkable activity against *Colletotrichum gloeosporioides*, their $IC_{50}$ values are respectively 4.05±0.46 μg/mL, 1.92±0.19 μg/mL, 3.82±0.09 μg/mL. Compound 02 showed excellent activity against *Botrytis* sp. ($IC_{50}$=3.93±0.80 μg/mL).

In present disclosure, the compounds (griseofulvin 4 position etherified derivatives) can be used to be fungicide against phytopathogenic fungi. These compounds can used to as main activity components which could be prepared to be some emulsion, hydrating agent, flowable agent, aqueous solution or their mixture as a preventive or direct antifungal agent against phytopathogenic fungi.

The invention claimed is:

1. Griseofulvin 4 position etherified derivatives, wherein chemical structures of the griseofulvin 4 position etherified derivatives are shown in a formula I below:

I

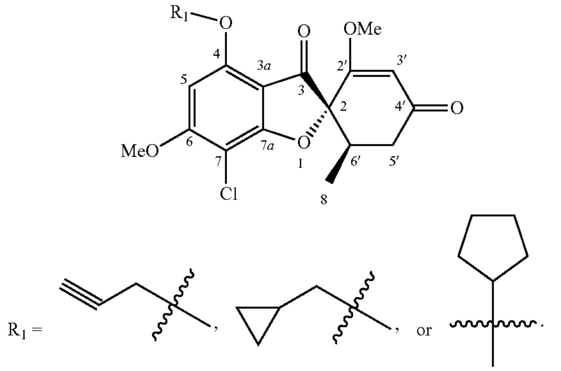

2. A preparation method of the griseofulvin 4 position etherified derivatives as claimed in claim 1, comprising:

with organic solvent and base, intermediate II reacted with different bromo compounds, griseofulvin 4 position etherified derivatives are obtained, wherein the different bromo compounds are propargyl bromide, cyclopropylmethyl bromide, and bromocyclopentane;

wherein a chemical structure of the intermediate II is expressed as follows:

II

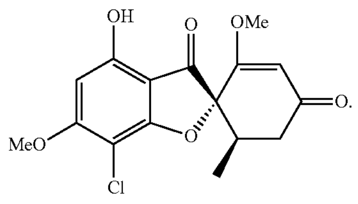

3. The preparation method as claimed in claim 2, wherein after the reacting is finished, a reaction mixture is obtained, and the preparation method specifically comprises: concentrating the reaction mixture and then purifying the reaction mixture after the concentrating by a column chromatography method, to thereby obtain the griseofulvin 4 position etherified derivatives.

4. The preparation method as claimed in claim 2, wherein the organic solvent is but not limited to acetone or tetrahydrofuran (THF) or their mixture.

5. The preparation method as claimed in claim 2, wherein the base is but not limited to $K_2CO_3$ or $Na_2CO_3$ or $Cs_2CO_3$.

6. A method for controlling phytopathogenic fungi, comprising: applying an effective concentration of the Griseofulvin 4 position etherified derivatives as claimed in claim 1 to a plant infected by the phytopathogenic fungi.

7. The application as claimed in claim 6, wherein the phytopathogenic fungi includes one or at least two selected from the group consisting of *Cytospora* sp., *Alternaria solani Sorauer, Alternaria* alternate, *Botrytis* sp., *Botrytis cinerea* Pers., *Colletotrichum gloeosporioides*, and *Botryosphaeria dothidea.*

8. The method as claimed in claim 6, wherein the effective concentration is 100 micrograms per milliliter (ug/mL).

* * * * *